(12) United States Patent
Nelson et al.

(10) Patent No.: US 11,851,644 B2
(45) Date of Patent: Dec. 26, 2023

(54) MARINE BACTERIA FORMULATION USEFUL IN AQUACULTURE

(71) Applicant: University of Rhode Island Board of Trustees, Kingston, RI (US)

(72) Inventors: David R. Nelson, Wakefield, RI (US); Jason LaPorte, Riverside, RI (US); David C Rowley, Wakefield, RI (US); Marta Gomez-Chiarri, Kingston, RI (US)

(73) Assignee: University of Rhode Island Board of Trustees, Kingston, RI (US)

( * ) Notice: Subject to any disclaimer, the term of this patent is extended or adjusted under 35 U.S.C. 154(b) by 401 days.

(21) Appl. No.: 16/866,265

(22) Filed: May 4, 2020

(65) Prior Publication Data
US 2020/0347345 A1    Nov. 5, 2020

Related U.S. Application Data

(60) Provisional application No. 62/842,282, filed on May 2, 2019.

(51) Int. Cl.
*C12N 1/20*    (2006.01)
*A61K 35/741*    (2015.01)

(52) U.S. Cl.
CPC .............. *C12N 1/20* (2013.01); *A61K 35/741* (2013.01); *C12N 2500/05* (2013.01); *C12N 2500/32* (2013.01); *C12N 2500/74* (2013.01)

(58) Field of Classification Search
None
See application file for complete search history.

(56) References Cited

U.S. PATENT DOCUMENTS

| | | | |
|---|---|---|---|
| 6,376,229 B2 * | 4/2002 | Morris | C12N 1/04 435/307.1 |
| 9,131,687 B2 | 9/2015 | Kolter et al. | |
| 9,868,957 B2 | 1/2018 | Qvit-Raz et al. | |
| 2018/0296657 A1 | 10/2018 | Barbet et al. | |

OTHER PUBLICATIONS

M. Karim et al., "Probiotic Strains for Shellfish Aquaculture: Protection of Eastern Oyster, Crassostrea Virginica, Larvae and Juveniles Against Bacterial Challenge," J of Shell Res, (2013) 32:2, 401-408.
W. Zhao et al., "Contributions of tropodithietic acid and biofilm formation to the probiotic activity of Phaeobacter inhibens," BMC Microbiol. (2016) 16:1.
G. Richards et al. "Mechnisms for Pseudoalteromonas piscicida-Induced Killing of Vibrios and Other Bacterial Pathogens," Appl Environ Microbiol (2017) 83:e00175-17.

* cited by examiner

*Primary Examiner* — Vera Afremova
(74) *Attorney, Agent, or Firm* — Milstein Zhang & Wu LLC; Duan Wu, Esq.

(57) ABSTRACT

The invention provides a method and related compositions for preparing an effective probiotic bacteria formulation that can be stored, transported and used for protecting a variety of marine organisms against infection by potential pathogens.

20 Claims, 7 Drawing Sheets

- mYP30

CFU/ml = 2.0x10$^9$

OD600 = 0.787

ZOI vs. RE22 = 0.4mm

- mLB30

CFU/ml = 2.2x10$^9$

OD600 = 1.323

ZOI vs. RE22 = 1.7mm

FIG. 5

• mYP30

(1:1 ASW, 4°C four weeks)

| CFU/ml | ZOI |
|---|---|
| $3.5 \times 10^8$ | 0.0mm |

Recovered at room temperature
4h = $4.2 \times 10^8$  0.1mm
24h = $5.3 \times 10^8$  0.4mm

• mLB30

(1:1 ASW, 4°C four weeks)

| CFU/ml | ZOI |
|---|---|
| $5.7 \times 10^8$ | 0.8mm |

Recovered at room temp.
4h = $5.8 \times 10^8$  1.4mm
24h = $7.4 \times 10^8$  1.7mm

FIG. 6

| Time (days) | Conditions[a] | | | | | | | |
|---|---|---|---|---|---|---|---|---|
| | LB-ASW 20°C | | LB-ASW 4°C | | YP-ASW 20°C | | YP-ASW 4°C | |
| | CFU/ml[b] | ZOI[c] (mm) | CFU/ml[b] | ZOI[c] (mm) | CFU/ml[b] | ZOI[c] (mm) | CFU/ml[b] | ZOI[c] (mm) |
| 0 | $1.98 \times 10^9$ | 7.8 | $1.98 \times 10^9$ | 7.8 | $1.74 \times 10^9$ | 7.7 | $1.74 \times 10^9$ | 7.7 |
| 7 | $2.33 \times 10^9$ | 8.0 | $1.40 \times 10^9$ | 4.3 | $1.67 \times 10^9$ | 7.8 | $1.47 \times 10^9$ | 3.9 |
| 18 | $4.23 \times 10^7$ | 1.0 | $4.27 \times 10^7$ | 0 | $2.40 \times 10^7$ | 0.9 | $1.53 \times 10^6$ | 0 |
| 25 | $8.66 \times 10^6$ | 0 | $1.76 \times 10^4$ | 0 | $1.80 \times 10^6$ | 0 | $3.00 \times 10^3$ | 0 |

FIG. 8

MARINE BACTERIA FORMULATION USEFUL IN AQUACULTURE

CROSS-REFERENCE TO RELATED APPLICATIONS

This application claims priority to and the benefit of U.S. provisional patent application Ser. No. 62/842,282, filed May 2, 2019, which application is incorporated herein by reference in its entirety.

STATEMENT REGARDING FEDERALLY SPONSORED RESEARCH OR DEVELOPMENT

This invention was made with government support under grant number NA18NMF4270193 awarded by NOAA and grant numbers 2012-38500-19656, 2014-38500-22228, 2016-67016-24905, 2019-67016-29868 and 2019-70007-30416 awarded by USDA/NIFA. The government has certain rights in the invention.

FIELD OF THE INVENTION

The invention relates to formulations of Gram-negative and/or probiotic bacteria formulation suitable for use in aquaculture systems, e.g., for the protection of oyster larvae.

BACKGROUND OF THE INVENTION

Shellfish and finfish have long become an important part of the human diet. Besides fishing and trapping, people also have used farming technologies to produce shellfish, finfish and other aquatic species as food source. As a result, aquaculture including mariculture, where sea or sea-like salt water is used, has become an indispensible part of the food production chain with tremendous economic value. In recent years, aquaculture produced more than half of all finfish and shellfish consumed. In United States alone, more than 285 M tonnes of seafood was harvested through aquaculture in 2015, worth more than $1.4 billion USD. With the globe facing an ever-growing human population and continued loss or pollution of vast quantities of farmland and previously clean water bodies, the quality and quantity of food production from aquaculture and mariculture in particular have become increasingly important. U.S. marine aquaculture production increased, on average, by 3.3% annually between 2009 and 2014. However, in 2016, the U.S. still had a trade deficit in seafood in the sum of $14 billion USD. Therefore, improving seafood cultivation could not only alleviate ecological stress on the oceans of the world, but also improve multilateral economic relations amongst nations.

Among the various species cultivated by aquaculture, bivalve products harvested in the U.S. came to worth of about $200 million USD in 2013. A popular bivalve aquaculture product has been oysters. In 2017, in the U.S. state of Rhode Island alone, about 8.4 million oysters were harvested, a 13.6-fold increase from 2016. The dominant species of oyster in Rhode Island is the Eastern Oyster (*Crassostrea virginica*). Eastern Oysters, as well as many other kinds of oysters, are supplied to oyster farmers by hatcheries as juveniles ("seed" oysters) for large-scale settlement and cultivation in the farms. Therefore, any problems at the hatcheries or during the course of transportation could lead to shortages in the supply of "seed" oysters to the farmers.

One of the problems that can severely affect the health of oysters including these larval and seed oysters out of hatcheries is bacterial infections caused by pathogens such as two pathogenic bacteria often found on many coasts of the world: *Vibrio tubiashii*, some strains renamed *Vibrio coralliilyticus*, (hereinafter collectively referred to as the "Vibrio species" or "Vibrio family"); and *Aliiroseovarius crassostreae*, formerly known as *Roseovarius crassostreae*.

In addition to affecting oyster productions, several Vibrio species cause significant disease losses to other marine aquaculture as well: for example, *V. anguillarum* is known to infect fish, mollusks, and crustaceans; *V. coralliilyticus* infects mollusks (and coral); *Vibrio parahaemolyticus* infects crustaceans (i.e. shrimps); and *Vibrio tubiashii* also infects mollusks.

We have previously isolated two probiotic bacteria that have shown to protect oyster larvae and juveniles against infections by bacterial pathogens *Vibrio tubiashii* and *Aliiroseovarius crassostreae* (then known as *Roseovarius crassostreae*). One of the two probionts is gram-negative and is identified as *Phaeobacter inhibens* S4. The second probiont is gram-positive and is identified as *Bacillus pumilus* RI06-95. See M. Karim et al., J of *Shell Res*, (2013) 32:2, 401-408. In a series of further investigations, we first described and demonstrated that *P. inhibens* strain S4 secretes the antibiotic tropodithietic acid (TDA), is an excellent biofilm former, and increases oyster larvae survival when challenged with bacterial pathogens (Zhao et al., *BMC Microbiol*. (2016) 16:1). More recently, we demonstrated that quorum-quenching activity of acyl homoserine lactones by *P. inhibens* represses virulence gene expression by shellfish pathogen *V. coralliilyticus*, a *Vibrio* species (Zhao et al., *Appl Envir Microbiol*, (2019) 85: e01545-18) and immunomodulation (Modak, Ph.D. Thesis, *University of Rhode Island*, 2019).

Our further hatchery experiments also showed that addition of the two probiotic strains (*P. inhibens* and *B. pumilus*) decreases oyster larval mortality and *Vibrio* species densities in hatcheries without affecting oyster larval growth (Sohn et al., *J. Shellfish Res*, (2016) 35:307-317). We also demonstrated the efficacy of using such probiotics in preventing *Vibrio* species infections in the larviculture of different bivalve shellfish species such as scallop and quahog (Sohn et al., *J. Shellfish Res*, (2016) 35:319-328.)

However, *P. inhibens* represents gram-negative, non-spore-forming bacteria that do not survive drying procedures in high enough densities to be commercially viable for applications in aquaculture or mariculture. Accordingly, there is an unfulfilled need for antibacterial formulations that can be delivered to various hatchery destinations so that they will survive long enough in storage and transportation, and in high enough density to be economical and effective while being easy to use for the hatchery personnel.

SUMMARY OF THE INVENTION

The present invention provides a formulation or composition where one or more bacteria, preferably marine bacteria, are stored and transported in a medium. In a preferred embodiment, the bacteria are first grown to high density in the medium before nutrient contents are diluted to a level that only sustains bacteria's survival but not high-rate growth, while salt level is maintained at an elevated level. Preferably, the bacteria grown and stored according to methods of the invention are probiotic or have antibiotic capacities to protect a marine species, preferably of economic value.

In one aspect, the invention provides a method of making a heterotrophic marine bacterial composition. The method includes a step of growing a population of marine bacteria to high density in a medium that contains one or more sources for multiple amino acids, and optionally vitamins, and mineral salts. In a subsequent step, the bacteria-bearing medium is added both of the following: (i) water to dilute the source(s) for amino acids to a lower concentration and (ii) a sufficient amount of salt(s), e.g., sea salts, to maintain a total salt concentration (e.g., at or above 2.0, 2.5, 3.0, or 3.5%) in order to slow down or halt further bacterial growth and to preserve bacterial vitality such that, after 1, 2, 3, 4, 5, or even 6 weeks, at least about 50%, 70%, or 80% of the probiotic bacteria population remain viable and retain their probiotic capabilities. In an embodiment, the second step is accomplished through addition of sterile artificial seawater or sterile natural seawater to the bacteria-bearing medium.

The formulated probiotic composition of the present invention can be used in a method to reduce or prevent mortalities due to bacterial pathogens in mariculture and aquaculture in general. The invention can be used to protect populations of various marine species including their larviculture, post-larval (juvenile) population, and adult population.

Accordingly, in one aspect, the invention provides a heterotrophic marine bacterial composition, preferably probiotic or antibiotic, where a population of marine bacteria is introduced into a medium containing one or more sources for making multiple amino acids where the medium is at a final salt concentration of at least 20 or preferably 25 g/L, in other words, at least 2.0% or preferably 2.5% (i.e., a salinity of 20 or 25 PSU and above), and where the bacteria are at a density of at least about $1\times10^6$, or $1\times10^7$ CFU/ml (and optionally, no more than $1\times10^{11}$, $1\times10^{10}$, $1\times10^9$, or $1\times10^8$ CFU/ml) and the one or more sources for multiple amino acids and optionally vitamins are at low concentrations (also referred to as "storage" concentrations herein) limiting or slowing bacterial growth yet sustaining bacterial vitality. In a preferred embodiment, probiotic bacteria are first grown in the medium to the desired high density for them to be effectively probiotic when they are administered to a host (which would likely involve some dilution), before a salt-containing water is added to dilute the one or more sources of multiple amino acids and optionally vitamins (e.g., at least one of carbon and nitrogen sources) to lower concentrations, i.e., the storage concentration: e.g., a peptone or tryptone at a concentration of no more than about 7.5 or 5.0 g/L, and yeast extract at a concentration of no more than about 3.0 or 2.5 g/L. In a feature, the bacterial population does not exceed $1\times10^6$, $1\times10^7$, $1\times10^8$, $1\times10^9$, or $1\times10^{10}$ CFU/ml in concentration after 7 or preferably 14 days, e.g., at room temperature.

The bacterial compositions of the invention may include bacteria that are *Proteobacteria*. In various embodiments, the bacteria may belong to the *Roseobacter* clade, more specifically, the Rhodobacteraceae family, and even more specifically, the *Phaeobacter* genus. In a preferred embodiment, the bacteria are *Phaeobacter inhibens*. In other embodiments, the bacteria belong to the Pseudoalteromonadaceae family. In another preferred embodiment, the bacteria are *Pseudoalteromonas piscicida*.

In another aspect, the invention provides a heterotrophic marine bacterial composition where a population of marine bacteria, preferably probiotic or with antibiotic capacities, are introduced into an aqueous medium with a total salt concentration of at least about 2.0 preferably 2.5%, wherein the bacteria are at a concentration of at least about $1\times10^6$, or $1\times10^7$ CFU/ml. With regard to nutrients, the medium further includes a carbon source and a nitrogen source for making multiple amino acids and hence proteins: both carbon and nitrogen sources and vitamins are at storage concentrations that will preserve at least about 50%, 70%, or 80% of the marine bacteria population for at least 1, 2, 3, 4, 5, or even 6 weeks, but not generate substantial further growth in the marine bacterial population at room temperature.

In an embodiment of the invention, the medium includes one or more ingredients selected from the group consisting of peptides, free amino acids, casein peptones, tryptone, casamino acids, yeast extract, carbohydrates, vitamins, a sulfur source, a phosphate source and mineral ions. In an embodiment, the medium includes a lysogeny broth (also known as Luria broth, Lennox broth or Luria-Bertani medium) and/or yeast extract.

In another aspect, the invention features a probiotic formulation comprising a population of *Phaeobacter inhibens* or *Pseudoalteromonas piscicida* in an aqueous medium at a concentration of at least about $1\times10^8$ CFU/ml; the medium includes a peptone or tryptone, yeast extract and natural or artificial sea water with a total salt concentration at about 2.0-3.5%; the peptone or tryptone is at a concentration of no more than about 7.5 or 5.0 g/L, and the yeast extract at a concentration of no more than about 3.0 or 2.5 g/L.

In a further aspect, the invention provides methods of protecting an aquaculture species from a pathogen, by administering to the species a marine bacterial composition prepared according to the principle of the invention. The aquaculture species includes species from shellfish and finfish, such as: oysters, clams, scallops, shrimps, lobsters and various finfish. Pathogens that are sensitive to TDA can be targeted using the present method, such as various *Vibrio* species, *Aliiroseovarius crassostreae*, formerly known as *Roseovarius crassostreae*, *Pseudomonas* species, *Photobacterium* species, *Flavobacterium* species, *Aeromonas* species, *Citrobacter* species, *Pasteurella* species, *Renibacterium* species, *Edwardsiella* species, *Francisella* species and *Moritella* species. Some gram-positive fish pathogens that may be targeted by the present invention include the *Mycobacterium* species and *Streptococcus* species.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 5 shows data on assay results on the probiotic activities of *P. inhibens* using the formulations according to embodiments of the invention. Specifically, some of the terms in the figures are defined as follows: "CFU"—colony forming units; OD600—optical density at 600 nm; and ZOI—zone of inhibition. The optical (OD600) and density measures (CFU/ml) were taken at 24-hour of growth in each medium. For the ZOI assay, cells taken at 24-hour of growth were spotted onto a plate with freshly spread *V. coralliilyticus* RE22 cells, and the ZOI was measured 24 hours later.

Notes on the table in FIG. 8: a: LB-ASW: Cells grown to stationary phase (~4×10$^9$ CFU/ml at 27° C.) in LB20, diluted 1:1 with sterile ASW, and then incubated without shaking at either 20° C. or 4° C.; YP-ASW: Cells grown to stationary phase (3.5×10$^9$ CFU/ml at 27° C.) in YP20, diluted 1:1 with sterile ASW, and then incubated without shaking at either 20° C. or 4° C.$^b$: Cell density determined by dilution and plating. All values are averages of 3 replicate samples.$^c$: ZOI determined by measuring the zone of inhibition from the edge of the JC3 colony to the edge of growth of the lawn of *Vibrio parahaemolyticus* PSU5579 after 24 hours of growth at 27° C.

DETAILED DESCRIPTION OF THE INVENTION

I. Definition

Unless otherwise noted, technical terms are used according to conventional usage. Definitions of common terms in molecular biology may be found, for example, in J. Krebs et al. (eds.), *Lewin's Genes XII*, published by Jones and Bartlett Learning, 2017 (ISBN 9781284104493); Robert A. Meyers (ed.), *Molecular Biology and Biotechnology: a Comprehensive Desk Reference*, published by Anmol Publications Pvt. Ltd, 2011 (ISBN 9788126531783); and other similar technical references.

As used in the specification and claims, the singular form "a", "an", or "the" includes plural references unless the context clearly dictates otherwise. For example, the term "a cell" includes a plurality of cells including mixtures thereof. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent," or "except for [a particular feature or element]," or "wherein [a particular feature or element] is not present (included, etc.) . . . ".

When a dimensional measurement is given for a part herein, the value is, unless explicitly stated or clear from the context, meant to describe an average for a necessary portion of the part, i.e., an average for the portion of the part that is needed for the stated purpose. Any accessory or excessive portion is not meant to be included in the calculation of the value.

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values >0 and <2 if the variable is inherently continuous.

As used herein, "about" means within plus or minus 10%. For example, "about 1" means "0.9 to 1.1", "about 2%" means "1.8% to 2.2%", "about 2% to 3%" means "1.8% to 3.3%", and "about 3% to about 4%" means "2.7% to 4.4%."

As used herein, "peptides" refers to short chains of amino acid monomers linked by amide bonds, branched or unbranched, generally contain about 50 or fewer amino acids. A molecule having more than about 50 amino acids are referred to as a protein. A relatively long and unbranched peptide chain can be called polypeptide. Peptides can be natural or synthesized.

As used herein, "peptone" refers to an early digestive product resulting from partial hydrolysis of proteins, such as casein. Peptones are generally water-soluble and contain a mixture of peptides and free amino acids. Tryptone is such a mixture of peptides and free amino acids normally as a result of digestion of casein by the protease trypsin.

As used herein, "high density" of a probiotic bacteria refers to a concentration where such bacteria can effect the intended health benefit to the host population, e.g., protection against a pathogenic infection, the actual value of which varies from species to species.

As used herein, "artificial seawater" refers to water with mineral salts, and optionally vitamins and small amounts of other compounds, dissolved therein to mimic natural seawater from a regular ocean where six major ions typically make up over 99% of the total dissolved therein: about 31% sodium ion (Nat), about 55% chloride anion (Cl$^-$), about 8% sulfate anion (SO$_4^{2-}$), about 4% magnesium ion (Mg$^{2+}$), about 1% calcium ion (Ca$^{2+}$), and about 1% potassium ion (K$^+$). While artificial seawater does not have to have all six ions/anions found in natural seawater, it should have at least a multiple of those. In general, the artificial seawater used in the present invention is commercially available and has a salt concentration of about 2.5-3.5% (or, a salinity of 25-35, i.e., 25-35 parts per thousand), and preferably about 3.0-3.5% (i.e., preferably a salinity of 30-35).

As used herein, "sea salts" refers to a mixture of natural and/or manmade ingredients, mostly salts, that resemble or mimic what is found in common seawater after evaporation of the water; it contains multiple salts with sodium chloride being the principal component (typically over 85%). Other components of the sea salt can vary from less than 0.2% to close to 10% and include calcium, potassium and magnesium salts of chloride and sulfate with much smaller amounts of trace elements. Such a mixture is commercially available, for example, under the trademark Instant Ocean®, and is sometimes marketed for use in aquariums.

As used herein, "source(s) for multiple amino acids" refers to substances that provide the necessary nutrients for making more than one amino acid. About 500 naturally occurring amino acids are known and 20 appear in the genetic code. Because the key elements in most amino acids are carbon, hydrogen, oxygen and nitrogen, in an aqueous environment (i.e., with $H_2O$ in abundance), "source(s) for multiple amino acids" are basically a carbon source and a nitrogen source, optionally with additional sources for building side chains for some amino acids (e.g., a sulfur source). Examples of sources for multiple amino acids include and are not limited to: peptides, free amino acids, casein peptones, tryptone, casamino acids, yeast extract, carbohydrates, vitamins, a sulfur source, a phosphate source and minerals.

As used herein, the term "room temperature" refers to about 20-23.5° C.

As used herein, "marine bacteria" refers to bacteria that can survive in a marine-like environment, particularly, in water with salinity between 25 and 35, preferably about 35.

As used herein, "antibiotic" refers to a substance or its ability to inhibit the growth and/or destroy pathogenic microorganisms, in other words, an "antibiotic-producing" organism may be bacteriostatic (slows down bacterial growth) and/or bactericidal (kills bacteria).

As used herein, "probiotic" refers to a live microorganism or its ability to provide, when consumed in a sufficient amount, a health benefit to the host. In aquaculture, probiotics can be administered either as a food supplement or as an additive to the water. Probiotics may be useful in aquaculture for any of a number of reasons: enhancement of immune responses in host species (e.g., by provision of antibiotic substances), improvement in nutritional intake by host species (e.g., through provision of supplemental digestive enzymes or essential nutrients), inhibition of pathogenic bacteria's growth or virulence (e.g., through competition for space and resources), and improvement of water quality. A probiotic species can have antibiotic characteristic or capabilities. In addition to land animals, aquacultural species can also benefit from the use of probiotics, including but not limited to bivalves (e.g., oysters and scallops), fish (e.g., salmon, cod, trout, halibut, turbot, and catfish), and crustaceans (e.g., shrimp, *Artemia* spp., crabs, and lobsters).

*Phaeobacter inhibens* (*P. inhibens*), under the Rhodobacteraceae family, is a gram-negative alpha-*Proteobacteria* from the *Roseobacter* clade, and is representative of the clade's far-reaching probiotic benefits over many marine species that are of commercial importance. Several species in the *Roseobacter* clade exhibit inhibitory activity against a wide variety of marine pathogens, including *V. anguillarum, V. tubiashii* and *R. crassostreae*. See, D'Alvise et al., *PloS One*, (2012) 7(8):e43996; D'Alvise et al., *Appl Environ Microbiol*, (2010) 76(7):2366-2370; Karim et al., *J Shell Res*, (2013) 32(2):401-408. *Roseobacter* species are typically excellent biofilm formers, colonizing a variety of surfaces including the skin of finfish and the shells of shellfish (See, e.g., Belas et al., *J Bacteriol*, (2009) 191(14): 4502-4512). We have previously demonstrated that both capacities by *P. inhibens*: the biofilm formation and the secretion of the antibiotic TDA, contribute to its probiotic and inhibitory effects on potential pathogens to shellfish such as *V. tubiashii* RE22 (later renamed *V. coralliilyticus* RE22) (Zhao et al., *BMC Microbiol*. (2016) 16:1). More recently, we explored the mechanism by which *P. inhibens* represses virulence gene expression by shellfish pathogen *V. coralliilyticus*, a *Vibrio* species (Zhao et al., *Appl Envir Microbiol* (2019) 85: e01545-18). In other words, bacteria from the *Roseobacter* clade, as represented by a member of the *Phaeobacter* genus under the Rhodobacteraceae family, can serve as probiotic agents protecting both finfish and shellfish, including their seed, juvenile, adult populations and larviculture.

*Pseudoalteromonas piscicida* (*P. piscicida*), a Gram-negative Gamma-proteobacterium under the Pseudoalteromonadaceae family, targets a variety of pathogens such as *Vibrio parahaemolyticus, Vibrio vulnificus, Vibrio cholerae, Photobacterium damselae*, and *Shewanella algae* (Richards et al. *Appl Environ Microbiol* (2017) 83:e00175). Among those pathogens, *Vibrio parahaemolyticus* PSU5579, is a pathogenic bacterial strain that causes acute hepatopancreatic necrosis disease (AHPND) in white leg shrimp (*Litopenaeus vannamei*). We have shown that *P. piscicida* JC3 is capable of probiotic activity against PSU5579 and other AHPND-causing strains to protect shrimps against AHPND (Camm J and Nelson DR, unpublished data).

According to principle of the invention, a formulation that is suitable for long-term storage and transportation of heterotrophic (i.e., cannot manufacture its own food by carbon fixation and therefore derives its intake of nutrition from other sources of organic carbon), gram-negative, non-spore-forming bacteria is hereby disclosed to prepare compositions of marine bacteria, preferably, having probiotic and/or antibiotic effects over aquacultural species. Examples of such bacteria can be found in many places, such as, as described immediately above, in the *Phaeobacter* genus under the Rhodobacteraceae family of the *Roseobacter* clade, or in the *Pseudoalteromonas* genus under the Pseudoalteromonadaceae family of the piscicida species. Simply put, the bacterial composition is prepared by first growing a population of the bacteria in a nutrient-rich environment to high density before using saltwater to dilute the medium to a "storage" state where nutrients for the bacteria no longer support a high growth rate, or even a slow growth, thereby arresting the bacteria in a starved or semi-starved state. Our data have further indicated that our storage formulation, while maintaining the storage state, can keep most in the bacteria population alive for an extended period. Depending on the application of the present technology, marine bacteria can be stored for at least 1, 2, 3, 4, 5, 6 weeks or even longer, often at different temperatures and conditions.

Once the stored bacteria are ready to be used, the bacteria-containing storage medium can be simply administered/added to a population of intended hosts/recipients, e.g., an oyster larviculture, with or without further dilution. It is often important, in a probiotic application, for the administered probiotic agents to be in a relatively high concentration, as we have demonstrated, through a prior study, that biofilm formation can be critical for effective probiotic or antibiotic activities as the biofilm matrix creates a microenvironment within which antibiotic secretions can accumulate to reach a level that is high enough to inhibit pathogens (Zhao et al., *BMC Microbiol*. (2016) 16:1).

Accordingly, in a preferred embodiment, the probiotic bacteria stored in the formulation of the invention is administered at least 24 hours or even longer (e.g., 2, 3, 4, 5, 6, or 7 days) prior to the aquaculture species' exposure to the pathogen. That way, time is given for the probiotic bacteria to form biofilms or otherwise retain a spatial advantage over the invading pathogen, which can be fast-replicating, in order to protect the host/recipient species.

EXAMPLE 1

In the following example, growth conditions for a probiotic, marine bacterium *Phaeobacter inhibens* are first optimized before they are switched to storage conditions. The protocol described below produced a final product in early stationary phase *Phaeobacter inhibens* S4 cells cultivated in mLB30 or mYP30 solutions, diluted 1:2 in ASW, and stored at 4° C. in an airtight container in the dark. Specifically, the method included steps as follows:

1. Growth: *Phaeobacter inhibens* S4 strain was streaked for isolation on YP30 agar plate/dish (containing both yeast extract and peptone, see details below) and incubated at 27° C. for 24-48 hours. Then, an isolated *P. inhibens* S4 colony was inoculated into an LB30 (for "lysogeny broth") growth medium (see details below) and incubated at 27° C. with shaking until reaching high density, in this case, the optical density at 600 nm ($OD_{600}$) reaches 2.4-2.6 (approximately $2 \times 10^9$ CFU/ml).

2. Dilution: one part of the *P. inhibens* culture was then combined with one part of artificial seawater (ASW) (see details below).

3. Storage: the culture was then stored at 4° C. in an airtight container in the dark for up to six weeks.

For an application in an oyster hatchery, the bacteria formulation was taken out of storage, mixed, and added to the oyster culture water daily at a rate of 3 ml formulation per 100 L oyster culture water to reach a final concentration of $1-3 \times 10^4$ CFU/ml *P. inhibens*.

Specifically, the above-referenced media were prepared as follows:

mYP30 agar (per liter): 5 g peptone; 1 g yeast extract; 30 g Instant Ocean® salt (sea salts); and 15 g agar, titrated to pH 7.5.

mLB30 (per liter): 10 g tryptone; 5 g yeast extract; 30 g Instant Ocean® salt (sea salts), titrated to pH 7.0.

ASW (per liter): 30 g Instant Ocean® salt (sea salts), titrated to pH 7.5.

Because of the amount of sea salts included in the YP and LB media, they are also sometimes referred to as "mYP" or "mLB," respectively, where "m" stands for "marine." The peptone/tryptone and yeast extract contained here are considered good source for building multiple amino acids as they can serve as source of carbon and nitrogen and more. Their exact amounts used in the formulation can vary and be adjusted according to the need of the marine bacteria being grown, as long as the initial amounts/concentrations in step (1) allow the marine bacteria to grow to high density. Also, other ingredients can be part of the medium, as are conventional in preparing certain kinds of bacterial culture, without departing from principles of the invention. These optional ingredients include and are not limited to: a carbohydrate (e.g., glucose or galactose), a sulfur source (e.g., adenine sulfate or ammonium sulfate), a phosphate source, vitamins and minerals. For example, yeast extract can be included as part of the medium as an important source of vitamins and other small molecular-weight compounds as well as a source of amino acids, even if the medium has tryptone or peptone or any other hydrolyzed amino acid source. Yeast extract is a complex and widely used hydrolysate of yeasts; it provides nitrogenous compounds, carbon, sulfur, trace nutrients, phosphorus, vitamin B complex and other important growth factors, which are essential for the growth of diverse microorganisms.

The salt in the formulation can be one or more types of salts, e.g., a sodium salt such as NaCl. But a sea salt mix gives the preferred result for the invention. The concentrations of various ingredients of the above media can vary, but the key is the final, or the storage levels should be made to support the survival of most, or at least a third, of the bacteria population, without too much nutrient for further growth. In other words, in the storage stage, the bacterial culture should enter an arrested stage where growth is minimal or significantly slowed down, before being taken out of that stage and encouraged to multiply again. In this particular example, the storage concentrations of various ingredients are (after dilution by seawater): tryptone at about 5 g/L, yeast extract at about 2.5 g/L and total salts at about 30 g/L.

Figure 1:
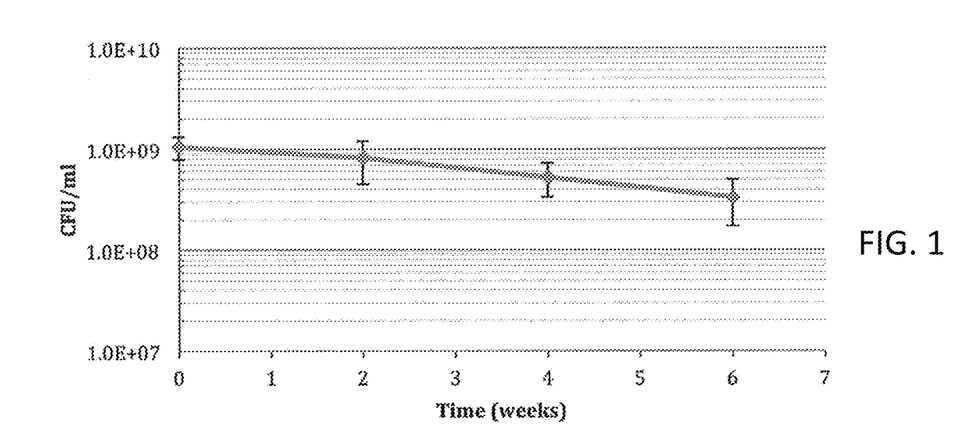
FIG. 1 shows data on the survival rate of *P. inhibens* using the formulation as time progresses, according to an embodiment of the invention.

The *P. inhibens* composition prepared according to the above protocol showed a shelf life of at least six weeks (FIG. 1). Specifically, *P. inhibens* cells grown and prepared as described above were incubated/stored at 4° C. in an airtight container in the dark. Samples of 50 μl were withdrawn every two weeks and intact/viable cell density was determined by serial dilution and plating on mYP30 agar plates. As shown in the chart, at two weeks, four weeks and even six weeks into storage, cell density remained well above $1 \times 10^8$ CFU/ml.

Figure 2:
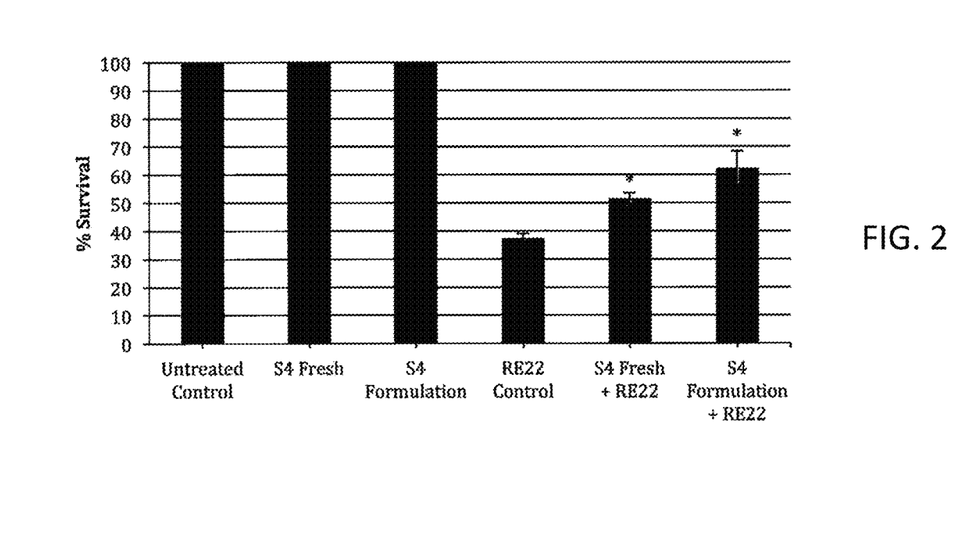
FIG. 2 shows data on survival of oyster larvae challenged with the marine pathogen *Vibrio coralliilyticus* RE22, with or without 24-hour pre-treatment with the probiotic formulation of *P. inhibens* according to an exemplary embodiment of the invention. In the controls, no probiotic treatment was given (*: Samples with oyster survival significantly higher than the RE22 control, $p<0.05$).

The *P. inhibens* composition prepared according to the above protocol demonstrated probiotic activities both in vitro (data not shown) and in vivo (FIG. 2) where this *P. inhibens* S4 formulation was shown to significantly improve the survival rate of oyster larvae challenged with the pathogen *Vibrio coralliilyticus* RE22. Specifically, oyster larvae (Eastern oyster, *Crassostrea virginica*) were incubated in the presence of either "fresh" or previously stored *P. inhibens* S4 formulation as described above ($1 \times 10^4$ CFU/ml) for 24 hours prior to being challenged with the pathogen *V. coralliilyticus* RE22 ($1 \times 10^5$ CFU/ml) for 24 hours. The "fresh" *P. inhibens* S4 was prepared by growing the bacteria to a density of $1-2 \times 10^9$ CFU/ml first and then diluting them to a density of $1 \times 10^4$ CFU/ml. Pre-treatment with the probiotic composition of the invention was able to improve larvae survival from under 40% to above 60%.

EXAMPLE 2

Figure 3:
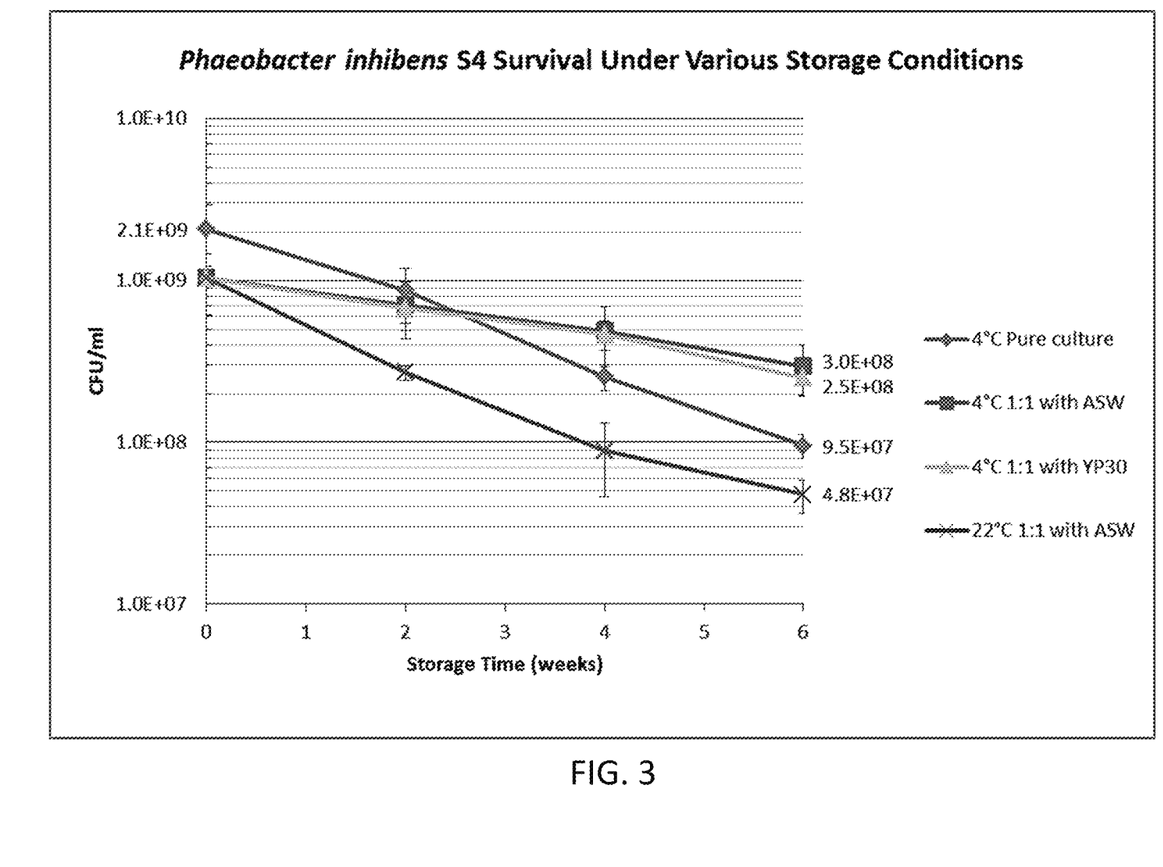
FIG. 3 shows the survival of *P. inhibens* in various formulations and under various storage conditions up to six weeks.

In this example, a few factors in the protocol for preparing the bacterial formulation of the invention in Example 1 were varied as well as the storage condition (FIG. 3). Of the four samples, three were stored at 4° C., and one was stored at 22° C. and showed most amount of cell loss, indicating a preferred storage temperature under 10° C. or 5° C., and preferably around 4° C. for storing *P. inhibens* in embodiments of the present invention.

Also, the diluent used in the "dilution" step of the protocol was varied, with the default being ASW. Specifically, in the "Pure culture" sample, no dilution took place, and the *P. inhibens* population dropped from $2.1 \times 10^9$ at the beginning of storage period to $9.5 \times 10^7$ after six weeks in storage. Using the mYP30 solution for the 1:1 dilution in the "dilution" step, however, the sample yielded highly comparable results, indicating that the storage concentrations for peptone/tryptone could be about 7.5 g/L and for the yeast extract at about 3.0 g/L, respectively. The ingredients for the YP30 solution (also known as mYP30) are the same as the YP30 agar listed in Example 1 minus the agar.

EXAMPLE 3

Figure 4:
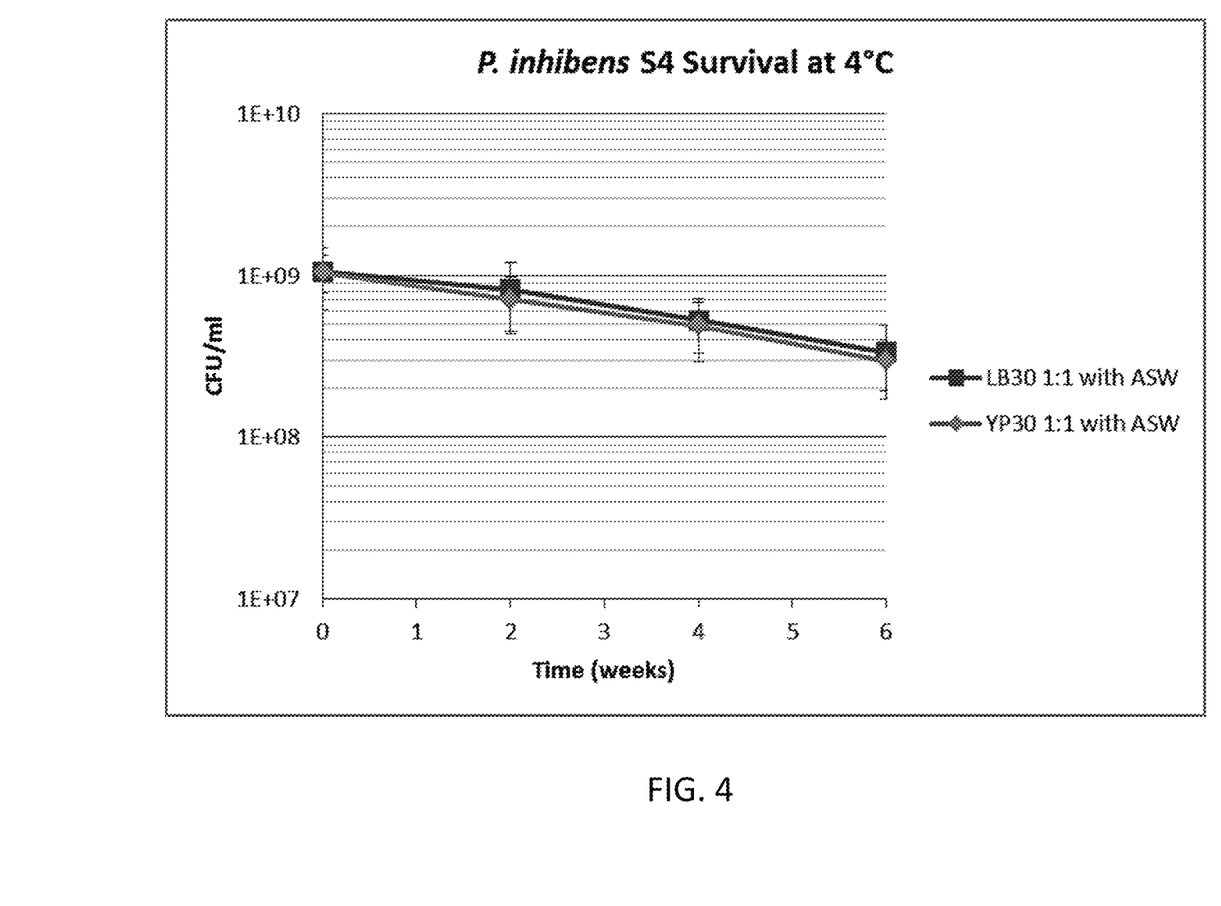
FIG. 4 shows data on the survival rate of *P. inhibens* using formulations according to different embodiments of the invention.
Figure 5:
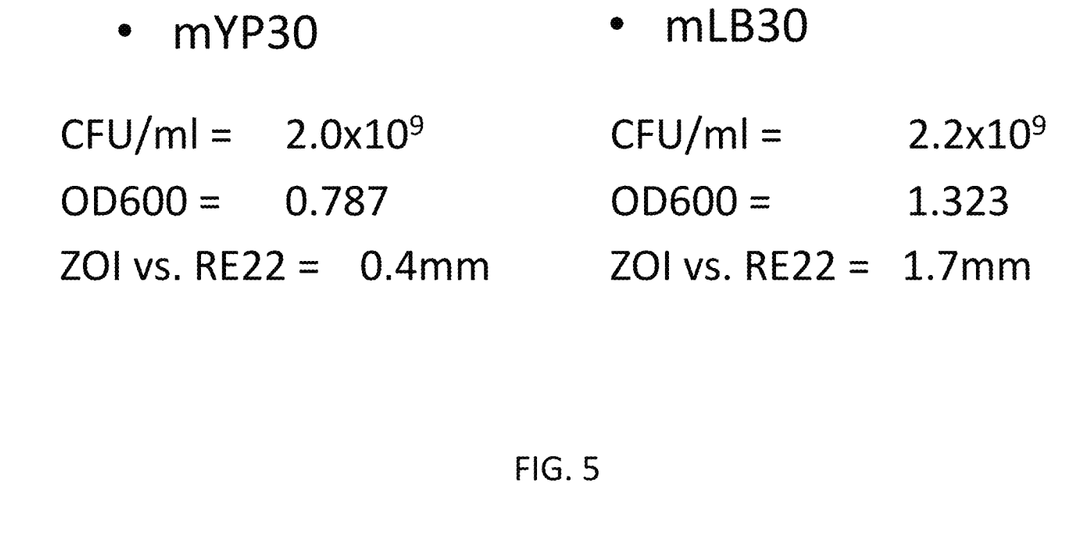
Figure 6:
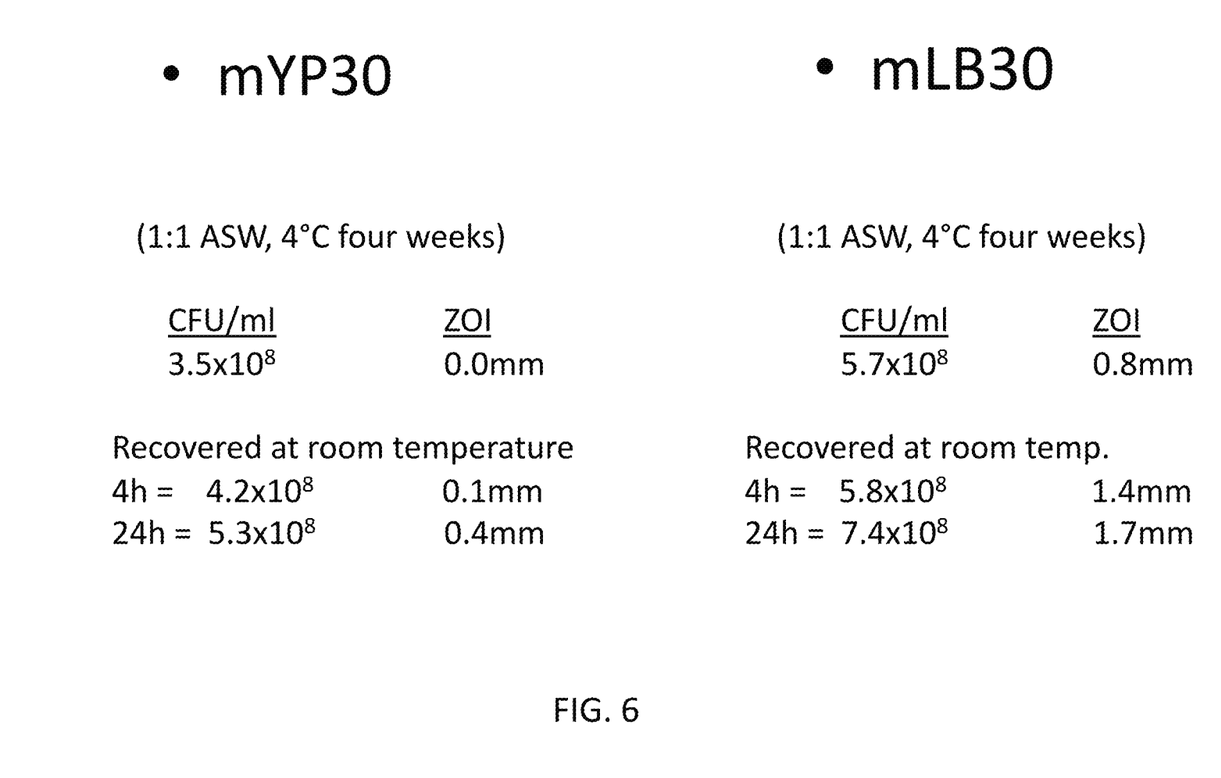
FIG. 6 shows data on assay results on the probiotic activities of *P. inhibens* stored for four weeks in the formulations according to embodiments of the invention.
Figure 7:
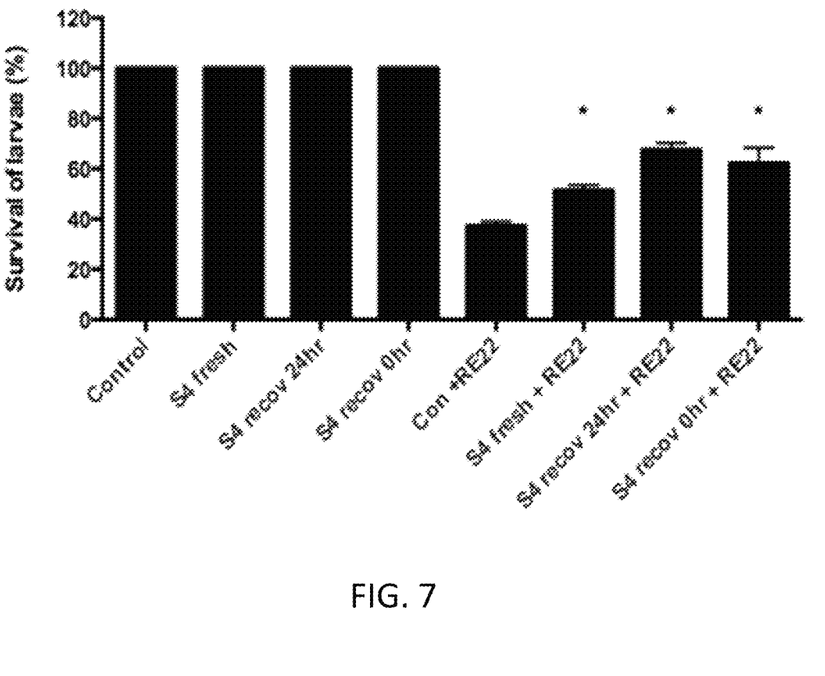
FIG. 7 shows the effects on survival of oyster larvae challenged with the marine pathogen *Vibrio coralliilyticus* RE22 with various treatment methods using an mLB30-based probiotic formulation of *P. inhibens* according to principles of the invention.

Here, comparison was made using either mLB30 (as in Example 1) or mYP30 for the initial "growth" step of the protocol described in Example 1. Comparable results were found in the amount of *P. inhibens* cells that survived after up to six weeks of storage at 4° C. for both samples (FIG. 4). However, samples using mLB30 exhibited greater probiotic activities than its counterpart using mYP30, based on zone of inhibition assay (ZOI) against the pathogen *V. coralliilyticus* RE22 (FIGS. 5 and 6). Allowing the probiotic composition to recover at room temperature after an extended period in storage appears to help the bacteria regain population growth and some probiotic capability in both the mLB30- and mYP30-based formulations (FIG. 6). The benefit of allowing some recovery time for the bacteria composition was again validated in an in vivo study in oyster larvae against the pathogen *V. coralliilyticus* RE22 (FIG. 7).

EXAMPLE 4

Figure 8:
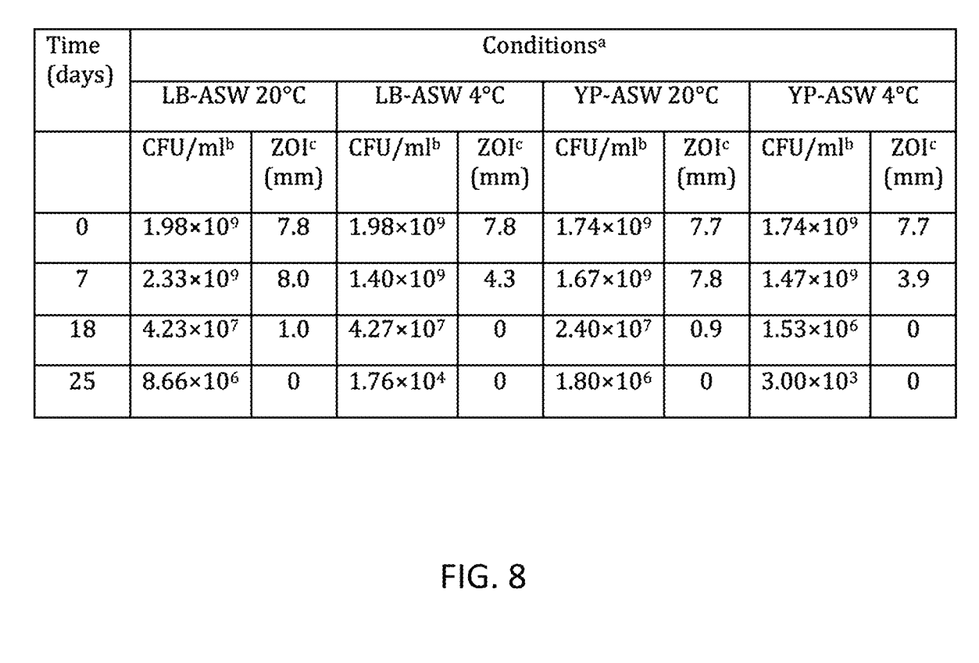
FIG. 8 summarizes data on survival and zone of inhibition (ZOI) for another probiotic bacterium *Pseudoalteromonas piscicida* JC3 using formulations according to different embodiments of the invention under different conditions.

In this example, a different probiotic bacterium, *Pseudoalteromonas piscicida* (*P. piscicida*) was tested of its strain JC3 for application of the inventive principle. Specifically, *P. piscicida* JC3 was examined for its survival and ability to produce antibacterial activities after various periods of storage in two media embodiments of the invention at two different storage temperatures (FIG. 8). One media embodiment was prepared by diluting LB20 solution 1:1 with ASW ("LB-ASW"), the other by diluting YP20 solution 1:1 with ASW ("YP-ASW"). Specifically:

LB20 solution (per liter): 10 g tryptone; 5 g yeast extract; 20 g Instant Ocean® salt (sea salts), titrated to pH 7.0.

YP20 solution (per liter): 5 g peptone; 1 g yeast extract; 20 g Instant Ocean® salt (sea salts), titrated to pH 7.5.

Unlike *P. inhibens* S4, *P. piscicida* JC3 appears to survive better at 20° C. than at 4° C. under storage condition. However, at least after 7 days in either storage media embodiments described above, at least 70% of the tested *P. piscicida* JC3 populations survived under both temperatures, and exhibited 100% of probiotic or antibiotic activity under 20° C.

While the present invention has been particularly shown and described with reference to the structure and methods disclosed herein and as illustrated in the drawings, it is not confined to the details set forth and this invention is intended to cover any modifications and changes as may come within the scope and spirit of the following claims. All publications and patent literature described herein are incorporated by reference in entirety to the extent permitted by applicable laws and regulations.

What is claimed is:

1. A method of making a heterotrophic and probiotic marine bacterial composition suitable for long-term storage and transportation, comprising:
    (a) growing a population of heterotrophic and probiotic marine bacteria to a high density of about $1\times10^6$ CFU/ml or higher in a broth medium containing at least one ingredient selected from the group consisting of peptone, tryptone, and yeast extract; subsequently
    (b) adding to the bacteria-bearing broth medium both (i) water between (1:1) and (1:2) (medium:water) by volume to dilute the medium to lower ingredient concentrations that sustain long-term bacterial vitality wherein any peptone or tryptone is diluted to at least about 1.7 g/L but no more than about 7.5 g/L and any yeast extract is diluted to at least about 0.3 g/L but no more than about 3.0 g/L in concentrations, and (ii) a sufficient amount of salt to maintain a total salt concentration at or above 2.0%, wherein further bacterial growth is slowed down but bacterial vitality is preserved and, after six weeks, at least about 50% of the bacteria population remain viable; and
    (c) storing and/or transporting the broth medium from step (b) wherein at least about 50% of the heterotrophic and probiotic marine bacteria composition contained therein remained viable.

2. The method of claim 1, wherein in step (b), the step of adding (i) water and (ii) salt to the bacteria-bearing broth medium comprises adding to the medium artificial seawater or natural seawater.

3. The method of claim 1, wherein the bacteria are probiotic or produce antibiotic.

4. The method of claim 1, wherein, in step (a), the at least one ingredient in the medium comprises a peptone or tryptone, and wherein, in step (b), the peptone or tryptone is diluted to a concentration of no more than about 5.0 g/L.

5. The method of claim 1, wherein, in step (a), the at least one ingredient in the medium comprises a yeast extract, and wherein, in step (b), the yeast extract is diluted to a concentration of no more than about 2.5 g/L.

6. The method of claim 1, wherein, in step (a), the medium comprises a lysogeny broth essentially comprising (i) tryptone or peptone, (ii) yeast extract and (iii) salt.

7. The method of claim 1, wherein, after step (b), the total salt concentration is about 2.5-3.5%.

8. The method of claim 1, wherein after step (b), the total salt concentration is about 30 g/L.

9. The method of claim 1, wherein, in step (a), the bacteria are grown to a concentration of about $1\times10^8$ CFU/ml or higher.

10. The method of claim 1, wherein, in step (a), the bacteria are grown to a concentration of about $1\times10^9$ CFU/ml or higher.

11. The method of claim 1, wherein the bacteria belong to the *Roseobacter* clade.

12. The method of claim 1, wherein the bacteria belong to the Rhodobacteraceae family.

13. The method of claim 1, wherein the bacteria are *Phaeobacter inhibens*.

14. The method of claim 1, wherein the bacteria are Proteobacteria.

15. The method of claim 1, wherein the bacteria are *Pseudoalteromonas* piscicida.

16. The method of claim 1, wherein in step (a), the broth medium further comprises at least another ingredient selected from the group consisting of a peptide, a free amino acid, casamino acid, a carbohydrate, a vitamin, a sulfur source, a phosphate source and a mineral ion.

17. A method of making a heterotrophic and probiotic marine bacterial composition suitable for long-term storage and transportation, comprising:
    (a) growing a population of heterotrophic and probiotic marine bacteria to a high density of about $1\times10^6$ CFU/ml or higher in a broth medium comprising at least one ingredient selected from the group consisting of tryptone, peptone, and yeast extract;
    (b) subsequently adding to the bacteria-bearing broth medium seawater between (1:1) and (1:2) (medium:seawater) by volume to dilute the medium to a lower ingredient concentration that sustains long-term bacterial vitality wherein any peptone or tryptone is diluted to about 5.0 g/L and any yeast extract is diluted to about 2.5 g/L in concentrations, and to maintain a total salt concentration between about 2.0% and about 3.5%, wherein further bacterial growth is slowed down but bacterial vitality is preserved and, after six weeks, at least about 50% of the bacteria population remain viable; and (c) storing and/or transporting the broth medium from step (b) wherein at least about 50% of the heterotrophic and probiotic marine bacteria composition contained therein remained viable.

18. The method of claim 17, wherein the medium in step (a) comprises a lysogeny broth essentially comprising (i) tryptone or peptone, (ii) yeast extract and (iii) salt.

19. The method of claim 17, wherein the bacteria belong to the *Roseobacter* clade.

20. The method of claim 17, wherein the bacteria are *Phaeobacter* inhibens.

* * * * *